s(12) United States Patent
Nicholls et al.

(10) Patent No.: US 8,777,899 B2
(45) Date of Patent: Jul. 15, 2014

(54) INJECTION APPARATUS

(75) Inventors: Clive Nicholls, Buckinghamshire (GB);
Robert Michael Wozencroft, Surrey
(GB); Jeremy Marshall, Oxford (GB)

(73) Assignee: Owen Mumford Limited, Oxfordshire (GB)

( * ) Notice: Subject to any disclaimer, the term of this patent is extended or adjusted under 35 U.S.C. 154(b) by 0 days.

(21) Appl. No.: 13/513,739

(22) PCT Filed: Dec. 6, 2010

(86) PCT No.: PCT/GB2010/052033
§ 371 (c)(1),
(2), (4) Date: Jul. 30, 2012

(87) PCT Pub. No.: WO2011/067615
PCT Pub. Date: Jun. 9, 2011

(65) Prior Publication Data
US 2012/0296276 A1  Nov. 22, 2012

Related U.S. Application Data

(60) Provisional application No. 61/266,669, filed on Dec. 4, 2009.

(30) Foreign Application Priority Data
Dec. 4, 2009  (GB) .................................. 0921295.2

(51) Int. Cl.
*A61M 5/31* (2006.01)
*A61M 5/50* (2006.01)

(52) U.S. Cl.
USPC .......................................... 604/110; 604/189

(58) Field of Classification Search
USPC ......... 604/110, 188–189, 192–193, 197–198, 604/208–210, 211, 224, 218
See application file for complete search history.

(56) References Cited

U.S. PATENT DOCUMENTS

| 5,417,326 | A  | * | 5/1995 | Winner ........................... | 206/365 |
| 5,743,889 | A  |   | 4/1998 | Sams |  |
| 7,678,084 | B2 | * | 3/2010 | Judson et al. .................. | 604/187 |
| 8,246,577 | B2 | * | 8/2012 | Schrul et al. .................. | 604/110 |
| 8,257,318 | B2 | * | 9/2012 | Thogersen et al. ........... | 604/211 |
| 2004/0069667 | A1 | * | 4/2004 | Tomellini et al. .............. | 206/364 |

(Continued)

FOREIGN PATENT DOCUMENTS

| EP | 0 554 996 A1 | 8/1993 |
| EP | 1463550 A2 | 10/2004 |

(Continued)

OTHER PUBLICATIONS

British Search Report, dated Mar. 31, 2010, from corresponding British application.

(Continued)

*Primary Examiner* — Quynh-Nhu H Vu
(74) *Attorney, Agent, or Firm* — Young & Thompson

(57) ABSTRACT

An injection apparatus includes a counter wheel (54) that is incremented by the dose delivery mechanism each time the device is fired. The apparatus includes a final dose disabling mechanism that prevents further usage once the final dose has been delivered. An anti-tamper feature is provided to prevent inadvertent or premature initialisation of the apparatus.

8 Claims, 5 Drawing Sheets

(56) References Cited

U.S. PATENT DOCUMENTS

| | | | |
|---|---|---|---|
| 2004/0215153 A1* | 10/2004 | Graf et al. | 604/218 |
| 2005/0001702 A1 | 1/2005 | Norton et al. | |
| 2005/0033224 A1 | 2/2005 | Kirchhofer et al. | |
| 2005/0090782 A1 | 4/2005 | Marshall et al. | |
| 2005/0165381 A1 | 7/2005 | Norrie et al. | |
| 2006/0276754 A1* | 12/2006 | Kronestedt et al. | 604/186 |
| 2007/0270762 A1 | 11/2007 | Kirchhofer et al. | |
| 2008/0033369 A1 | 2/2008 | Kohlbrenner et al. | |
| 2009/0134113 A1* | 5/2009 | Yan et al. | 215/228 |
| 2010/0209174 A1* | 8/2010 | Rauschert et al. | 401/126 |

FOREIGN PATENT DOCUMENTS

| | | |
|---|---|---|
| EP | 1 642 607 A1 | 4/2006 |
| EP | 1 414 507 B1 | 8/2006 |
| EP | 1 458 440 B1 | 4/2007 |
| GB | 2 443 390 A | 5/2008 |
| WO | 01/72361 A1 | 10/2001 |
| WO | 03/057285 A2 | 7/2003 |
| WO | 03/077973 A2 | 9/2003 |
| WO | 2006/045526 A1 | 5/2006 |
| WO | 2006/045528 A1 | 5/2006 |
| WO | 2006/069455 A1 | 7/2006 |
| WO | 2009/141003 A1 | 11/2009 |
| WO | 2009/141067 A1 | 11/2009 |

OTHER PUBLICATIONS

International Search Report, dated Jul. 27, 2011, from corresponding PCT application.

* cited by examiner

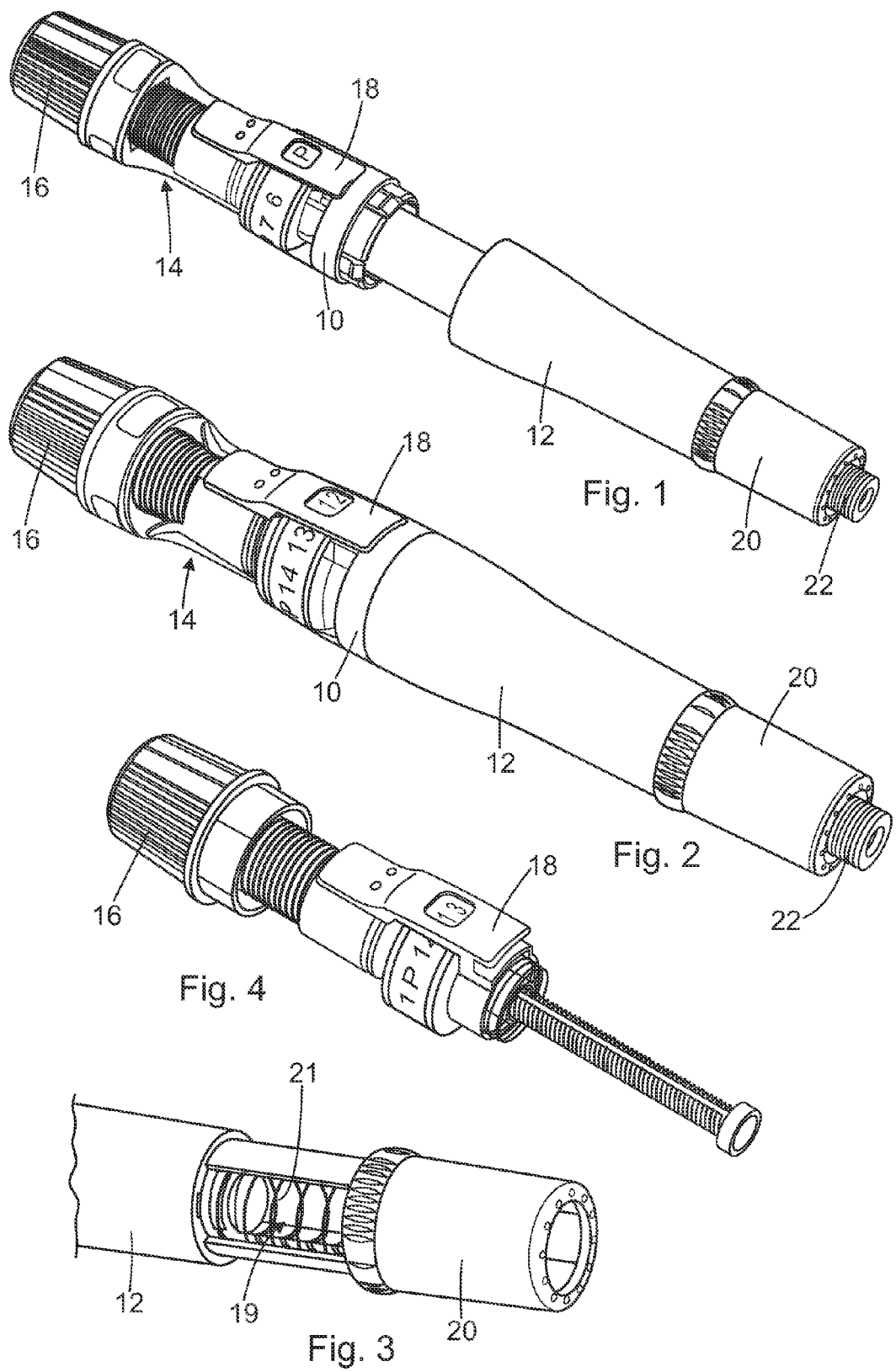

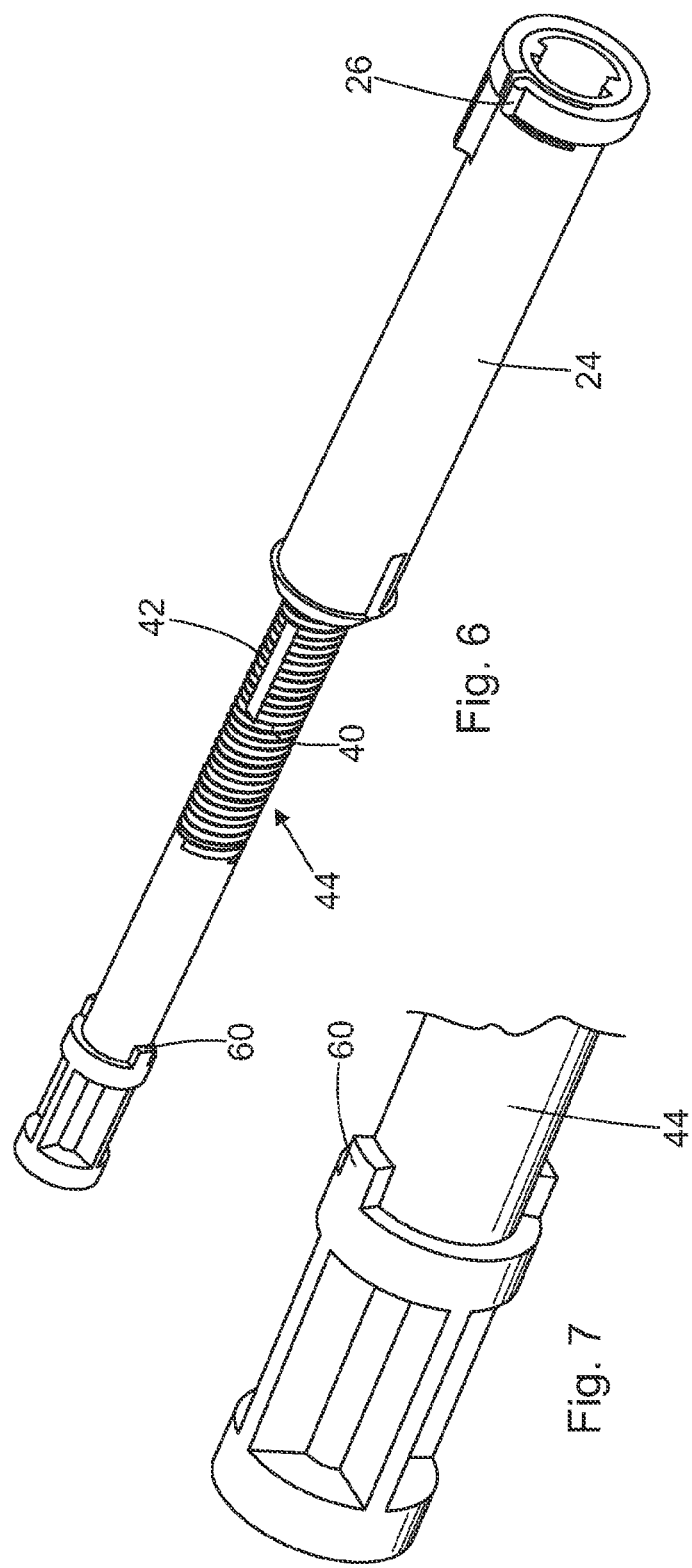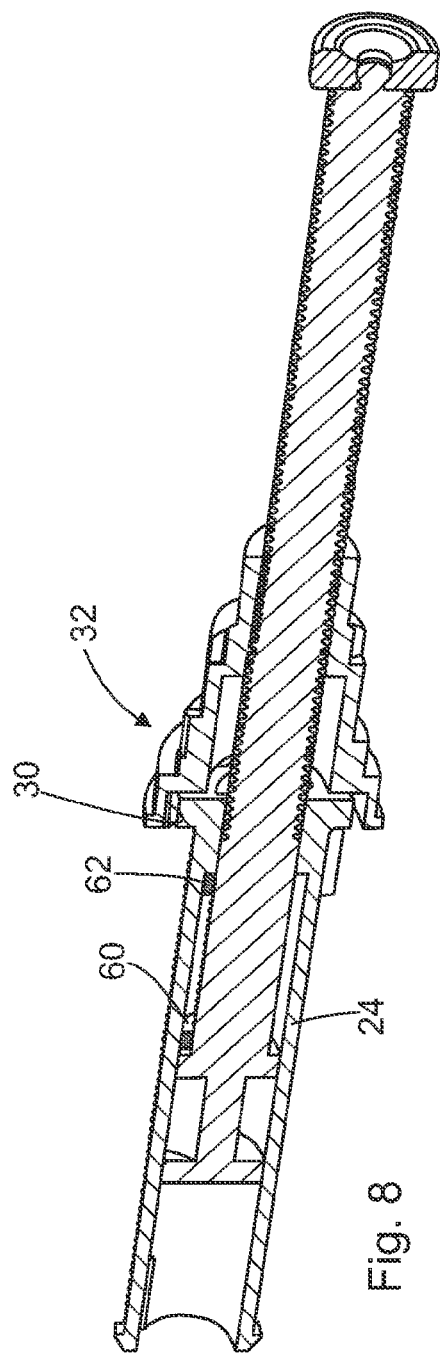

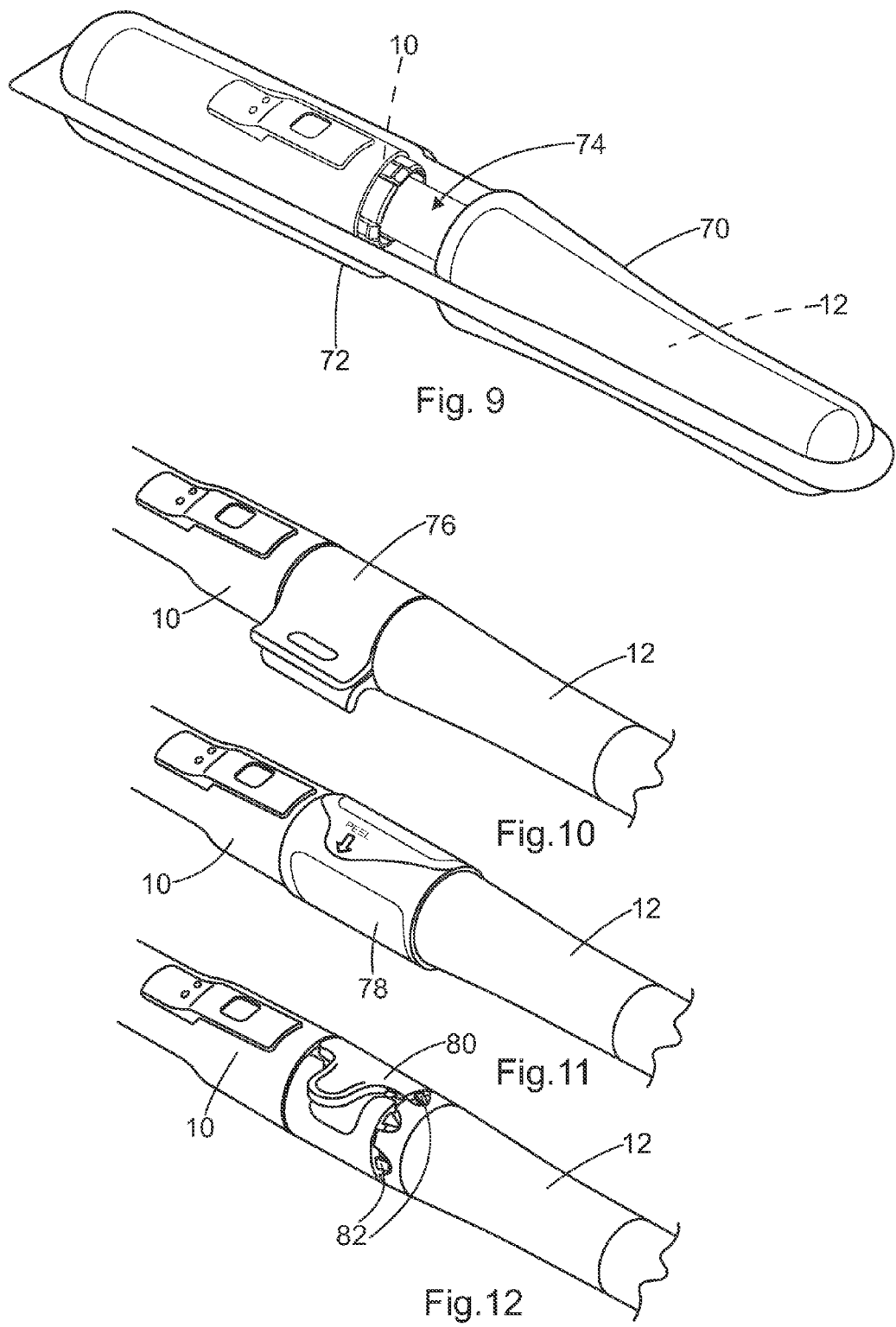

(a)　　　(b)　　　(c)

INJECTION APPARATUS

BACKGROUND OF THE INVENTION

1. Field of the Invention

This invention relates to injection apparatus, and in particular, though not exclusively, to injection apparatus designed to allow a number of doses to be delivered from a single cartridge or syringe over a period of time.

2. Description of the Related Art

In many therapies a drug needs to be injected at daily or other periodic intervals. A potential problem arises because the user may not recall clearly whether they have taken a particular dose. There is therefore a need in such apparatus to provide an increment counter, or day of the week indicator, which indicates whether they have taken the dose for a particular period. Also, where a fixed volume dose is delivered each time, it is highly desirable to be able to signal to the user when all useable doses have been taken from the device to prevent a user from inadvertently taking a nil or incomplete dose. Although it is common on variable dose devices to provide a counter display to allow a user to dial in the number of units of medicament they wish to inject, these displays only indicate the magnitude of the dose to be delivered, and return to zero on completion of an injection. They do not indicate a dose application count i.e. the accumulated number of injections that have been performed by the device.

In EP-A-1463550, we describe a dose application counter for an injection device having a dose counter member which has a lost motion connection to the dose setting element, so that, as a user sets the amount of the dosage volume prior to firing the device, the dose application counter is incremented by one count, irrespective of the number of units making up the dose. Although this is a good design, it increments the count on setting of the dose rather than actual delivery of the dose. It is possible therefore that if a user is distracted between the setting dose and delivering it, the dose application counter suggests that the dose for that period has already been taken. Also, after the device has been fired to deliver the final available dose, the dose setting knob can still be rotated to set a further dose even though subsequent firing of the device will not deliver a proper dose.

SUMMARY OF THE INVENTION

Accordingly, we have designed an injection device in which a counter member is incremented in response to movement of the drive member that delivers the does and which is therefore incremented by dose delivery rather than dose setting.

In one aspect this invention provides an injection apparatus including a drive arrangement actuatable to allow movement of a drive member to deliver a dose upon each such actuation, and a counter member drivingly connected to said drive member for being incremented by each dose delivery.

In this arrangement, a cumulative dose count may be kept by incrementing the counter by a single uniform amount indicative of a usage, irrespective of the dose magnitude.

Although the movement could be linear it is preferred for said drive member to be mounted for rotary movement and to rotate to deliver a dose. Thus the drive arrangement may include an elongate drive plunger threadedly engaged with said drive member and adapted to be advanced longitudinally to deliver a dose upon corresponding rotary movement of said drive member.

There are numerous ways in which actual delivery of a dose increments or trips or counter mechanism to increment by suitable motion transfer. For example, the counter member may comprise a counter wheel having a toothed surface meshing with an idler cog, with said drive member carrying one or more cog teeth for engaging the teeth of the idler cog to increment the counter wheel during each dose delivery. Although the drive member cog teeth could be in continuous engagement with the idler cog, or the counter wheel itself, said drive member cog teeth preferably engage the idler cog intermittently, once per dose delivery. It will be appreciated that incrementing may occur at any time during a dose delivery cycle, but it is preferred for said counter member to be incremented part way through the cycle. Alternatively, other arrangements may be used where movement of the dose delivery mechanism or a component thereof is used to increment a counter by one unit during or on completion of dose delivery. This could be tripped by interaction of the plunger with a counter, or by similar interaction between any one or more of the components in the dose delivery mechanism.

Conveniently, said drive mechanism includes a dose setting element for being manually twisted to energise an energy storage device associated with said drive member, and a releasable trigger for holding and releasing said drive member in and from its energised condition.

The injection apparatus may conveniently include a final dose arrangement for blocking movement of said dose setting element after said drive plunger has advanced to a final dose position, thereby to prevent further dose setting.

Where said drive arrangement includes a drive transfer element that rotates with, or is integral with, said dose setting element and is connectable to said drive member by a latching arrangement, the drive transfer element and the plunger may have associated therewith respective abutments that move into a blocking configuration when the drive plunger advances towards its final dose position, thereby substantially preventing rotational movement of the dose setting element and thus further dose setting movement.

The apparatus may be designed to deliver fixed volume doses, or it may be adapted to deliver doses of adjustable volume.

The final dose disabling feature may be used on devices that do not have a dose delivery counter. The invention therefore extends to an injection apparatus including a drive arrangement having a rotary drive gear threadedly engaged with an elongate threaded plunger to advance said elongate plunger to deliver a dose, a rotary dose setting element angularly movable against a bias from a rest position to an energised position in which it is in latching engagement with or latches with said rotary drive gear, a trigger arrangement adapted to hold and release the drive gear for rotary movement, wherein respective abutments associated with the drive plunger and the dose setting element move into a blocking configuration when said elongate plunger advances after successive doses to a final dose position, thereby preventing return of said rotary dose setting element to its latched, energised condition.

The abutments may comprise respective cooperable lugs on the drive plunger and on the dose setting element, which cooperate to constrain or limit rotation of said dose setting element.

Where the injection apparatus includes a housing having two relatively movable parts required to be moved relative to one another in an initialisation step prior to actuation to deliver a dose, for example to mix a multi-component drug, or to cock or to prime a device, it may include an anti-tamper arrangement to prevent said relative movement prior to release of the anti-tamper arrangement.

Said anti-tamper arrangement may typically comprise a removable package for containing at least part of said device and adapted to hold said movable parts against initialisation movement, prior to removal of said package.

Alternatively said anti-tamper arrangement may comprise a spacer element disposed to prevent said initialisation movement and removable from the apparatus.

The removable spacer element may comprise a tear off band, a tear off label, or a removable spacer element is integrally formed with one of said housing parts e.g. by moulding.

The invention also extends to an injection device comprising a housing having two relatively movable parts required to be moved relative to one another in initialisation step, prior to actuation to deliver a dose, and including an anti-tamper arrangement to prevent said relative movement prior to release of said anti-tamper arrangement.

The invention also extends to an injection device that is set or primed and which includes an externally visual indicator that displays a change in colour or other visual characteristics when said device is set or primed.

Whilst the invention has been described above, it extends to any inventive combination of the features set out above or in the following description, claims or drawings.

BRIEF DESCRIPTION OF THE DRAWING FIGURES

By way of example only, various embodiments of the invention will be now be described in detail, reference being made to the accompanying drawings in which:

FIG. 1 is a perspective view of an injection device in accordance with an embodiment of this invention in its as supplied form, prior to retraction of the housing to reconstitute the drug;

FIG. 2 is a view similar to FIG. 1 but showing the device after reconstitution of the drug and once two doses have been delivered;

FIG. 3 is a detailed view on the front end of the device of FIGS. 1 and 2 showing the collar in a forward position;

FIG. 4 is a view of the drive mechanism removed from the remainder of the device, with certain parts removed;

FIG. 6 is a detailed view on the plunger and ratchet drive shaft;

FIG. 7 is a detailed view on the aft end of the plunger;

FIG. 8 is a cross-sectional view through the ratchet drive shaft, drive plunger and the drive gear;

FIGS. 9 to 12 are views of various embodiments of an anti-tamper device that need to be removed prior to moving the housing from its extended position shown in FIG. 1 to that of FIG. 2;

Figure 5:
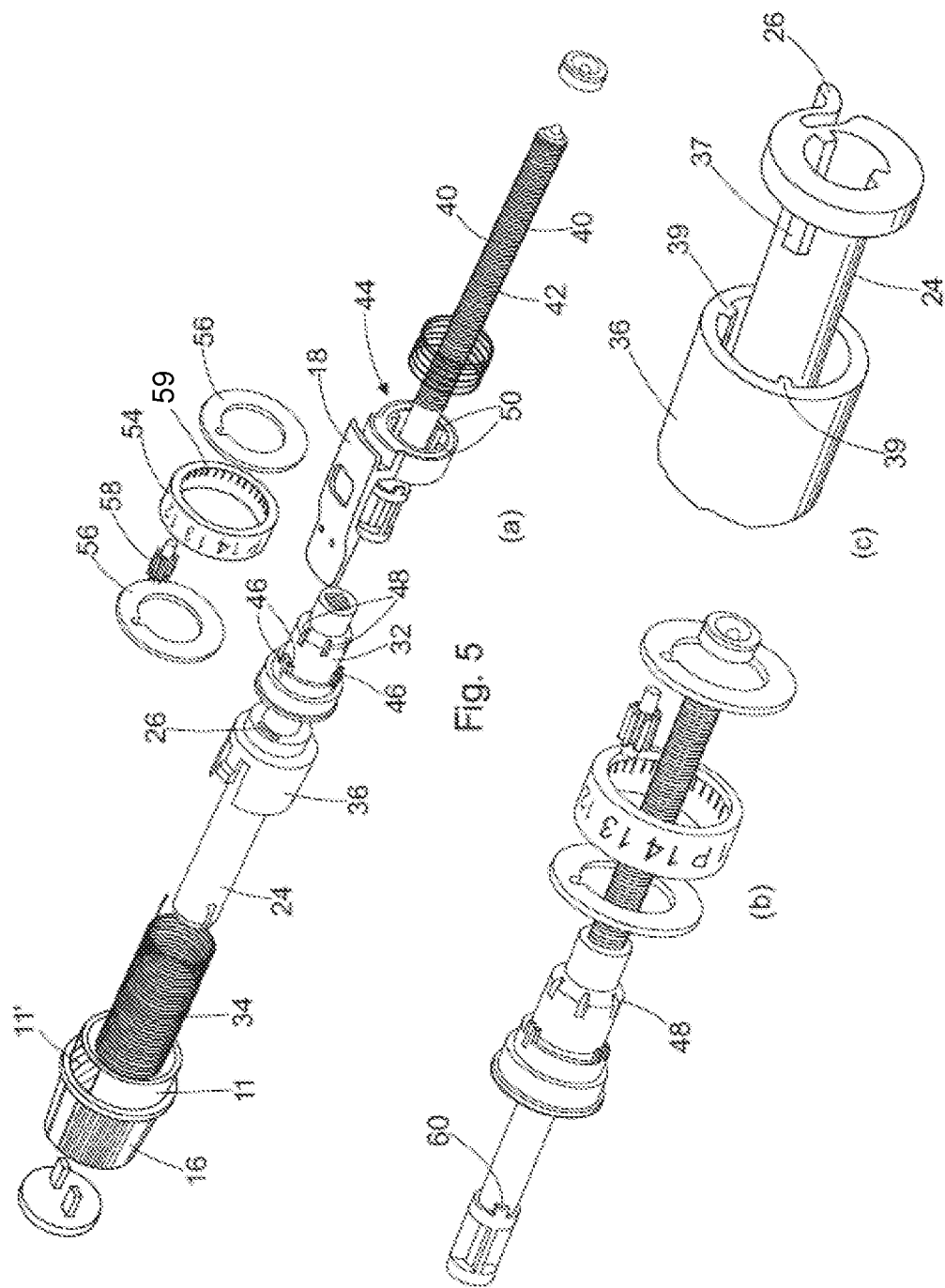
FIG. 5(a) is an exploded view of the drive mechanism, and FIGS. 5(b) and (c) are details thereof.
Figure 13:
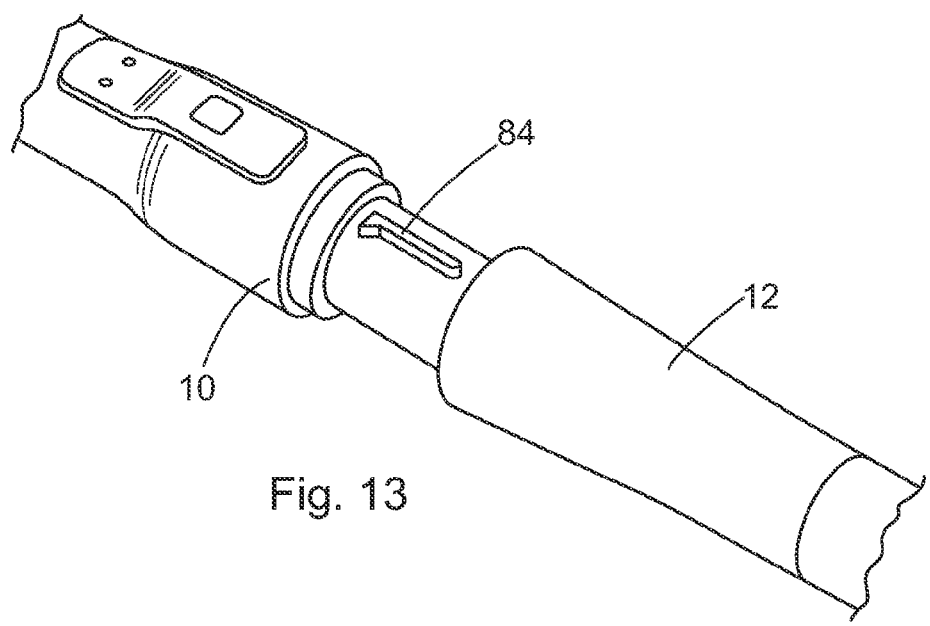
FIG. 13 is a detailed view on another form of anti-tamper feature.
Figure 14:
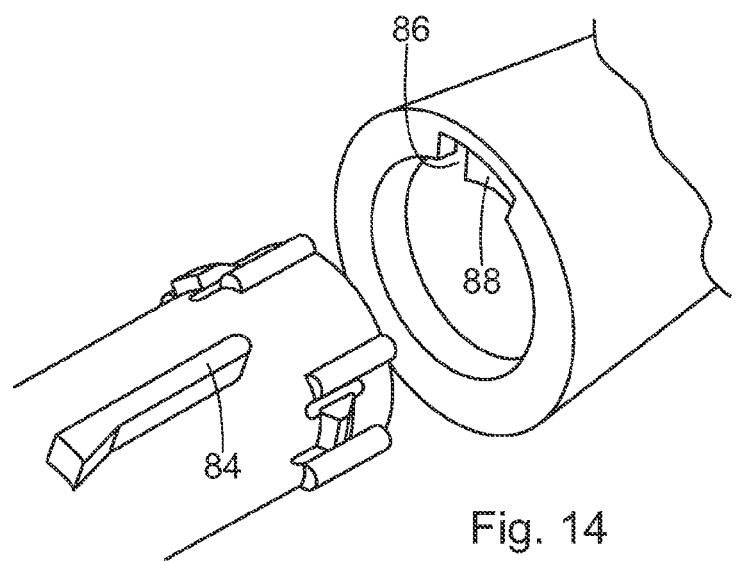
FIG. 14 is a detailed exploded view of part of the arrangement of FIG. 13.

FIGS. 15(a) to (c) are detailed views showing the anti-tamper feature of FIGS. 13 and 14 at various stages of operation.

DETAILED DESCRIPTION OF THE INVENTION

The embodiment of injection device illustrated in the drawings is designed for use with a medicament which is supplied as two components in unmixed form in a dual chamber cartridge of known type as described, for example, in our earlier application WO2007/132191. As supplied, the cartridge has two spaced bungs which define two separate chambers and the drug is mixed by driving the rearward bung forwardly so that it causes the forward bung to move forwardly to reveal and open a bypass slot and thereafter to force the fluid in the rear chamber into the front chamber to mix with the substance. In such devices an initial longitudinal movement is required to reconstitute the drug whereafter the normal metered doses are required. In the embodiment described below the doses are all of a uniform volume but it will be appreciated that the device may easily be modified to provide a facility to deliver doses of variable volume.

Referring to FIG. 1, the injection device comprises a housing made up of a rear part 10 and a forward part 12 telescopically mounted on a reduced diameter position of the rear part. A drive unit 14 is secured to the rear end of the rear housing part 10, and has a rotatable dial 16 at its rear end which is twisted to cock the device, and an actuator button 18 is slid forwardly to fire the device. The rotatable dial has a forward flange 11 that underlies the rear rim 13 of the outer shell 15 of the drive body. The rear rim is opaque apart from three transparent windows 17. The flange 11 of the dial has coloured patches 11' disposed so that, when the dial 16 is in the cocked position, the patches 11' align with the windows 17 to indicate a colour change to show readiness.

At the front end of the forward housing 12 there is a sprung loaded collar 20 having a bayonet interlock which allows it to be twisted and released forwardly under the influence of a spring 21 to reveal an inspection window through which the contents of the cartridge 19 may be viewed. The collar 20 also shrouds a needle hub (not shown) when attached to the threaded portion 22 at the front end of the cartridge.

Referring now to FIGS. 4 to 8, the drive mechanism will now be described in more detail. The dial 16 is fixed to the rear end of a ratchet drive shaft 24 for rotation therewith. At its forward end, the ratchet drive shaft carries a ratchet tooth 26 (see FIGS. 5(a), (c) and 6) that cooperates with corresponding inwardly facing latch teeth or recesses 30 on a drive gear 32 (see FIG. 8). A torsion spring 34 is anchored at its rear end to the dial 16 and at its forward end to a fixed support collar 36 which is fixed to the housing of the device. The ratchet drive shaft 24 is free to rotate inside the fixed support collar 36 but is limited to less than one turn of rotation by the interaction of an external rib 37 carried by the ratchet drive shaft 24 and internal ribs 39 carried within the support collar 36. The body 10 has a pair of inwardly directed splines (not shown) that cooperate with corresponding longitudinal grooves 40 formed in the threaded portion 42 of a plunger 44 to hold the plunger against rotation but to allow longitudinal movement thereof.

The drive gear 32 carries at 120° intervals around its surface three pairs of teeth 46 for incrementing a dose counter mechanism as to be described below. Forwardly of the teeth 46, the drive gear has a plurality of latching recesses 48 which cooperate with latching splines 50 on the forward end of the actuator button 18. The actuator button 18 is angularly fixed with respect to the housing and axially movable between a rear position in which the splines 50 engage the latch recesses 48 to prevent rotation of the drive gear to a forward position in which the drive gear is released.

The drive gear carries a threaded bore 52 that is threadedly engaged with the threaded portion 42 of the plunger 44 and so rotation of the drive gear advances the plunger by a preset amount. The threads on the plunger and the bore are multi-start, for example, 4-start threads.

In use, the device is cocked or energised by twisting the dial 16 through a third of a turn to wind up the torsion spring 34 and to rotate the ratchet drive shaft 24 until the ratchet tooth 26 locks in the respective latching recess 30 on the drive gear 32. The drive gear 32 in this position is held against rotation by the splines 50 on the actuator button.

In this condition the change in status is registered by the colour change in windows 17 adjacent the dial 16. Pushing the actuator button 18 forwardly releases the drive gear 32 so that it rotates with the ratchet drive shaft 24 under the influence of the torsion spring 34, advancing the plunger 44.

A counter wheel 54 is mounted concentrically with the drive gear 32 by means of spaced mounting plates 56 which also mount an idler gear 58 which meshes with an inner toothed track 59 on the inside of the counter wheel 54. The plates 56 are angularly fixed with respect to the housing and, as the drive gear 32 rotates, the teeth 46 trip the teeth of the idler cog 58 which in turn rotates the wheel by a uniform increment to register delivery of a dose and to keep a cumulative count.

As in seen in FIG. 7, the rear end of the plunger is formed with two lugs 60 which, as the plunger reaches its fully extended position engage or move between lugs 62 on the inside of the ratchet drive shaft 24 thereby restricting or preventing further rotation of the ratchet drive shaft relative to the plunger. This not only blocks further forward movement of the plunger, but also prevents the ratchet drive shaft from rotating relative to the housing. This means that the dial 16 is locked against rotational movement, subject to a small amount of backlash.

As can be seen from FIGS. 1 and 2, in order to prepare the device for injection, the forward housing part 12 needs to be slid rearwardly to be snap locked to the rear housing 10. In doing so, this causes the plunger to act on the rear bung (not shown) in the dual chamber cartridge 21 to effect mixing of the medicament. In order to provide a tamper evident feature and also to prevent inadvertent or premature mixing or reconstitution, the device of FIGS. 1 to 8 may be provided with an anti-tamper arrangement. Thus, in FIG. 9, the injection device is enclosed in plastics or similar removable casing halves 72, 74 which provide a recess 76, the opposed edges of which prevent telescopic movement of the forward and rearward housing parts.

In FIG. 10, a separate plastic component 76 is heat staked around the rear housing part 10, preventing telescopic movement of the housing parts until removal of the plastic component.

In FIG. 11, a peelable stick on label 78 is wrapped around the device to prevent the telescopic movement.

In FIG. 12, a moulded-end tear-off part 80 is integrally moulded with the front housing 12 and designed to be ripped off. The adjoining region between the tear-off part of the front housing may have recesses 82 to prevent sharp edges from being exposed.

Figure 15:
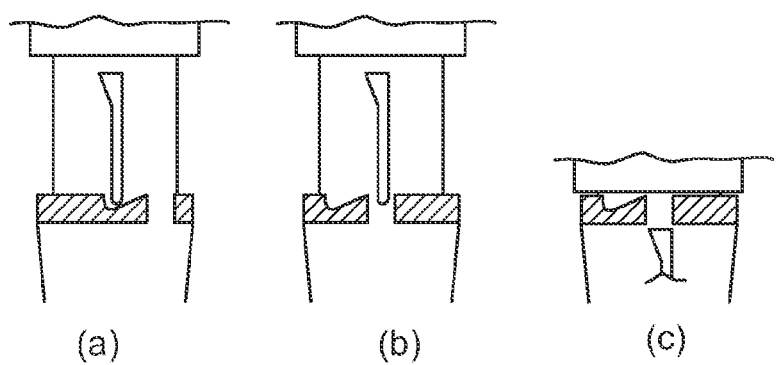

Turning now to FIGS. 13 to 15, in this arrangement a raised leg 84 is formed on the rear housing part 10 and cooperates with a profiled slot 86 in the rim of the forward housing part 12. In this arrangement the slot 86 is profiled so as to have a camming surface 88 up which the forward part of the leg 84 rides during initial turning movement to provide a resilient detent action (FIGS. 15(a) to 15(b)). Having ridden up the cam surface 88 the forward part of the leg 84 is aligned with the main portion of the slot 86 so that the forward housing part 12 can be slid telescopically back to meet an opposed surface of the rear housing part. The leg 84 widens towards its rear end so that, having moved to the telescoped position shown in FIG. 2 (FIG. 15(c)) it snaps irreversibly into the slot so it is not then possible to slide the forward housing part 12 forwardly.

The invention claimed is:

1. An injection apparatus including
a drive arrangement having a rotary drive gear threadedly engaged with an elongate threaded plunger to advance said elongate plunger to deliver a dose;
a rotary dose setting element angularly movable against a bias from a rest position to an energized position in which it latches with said rotary drive gear; and
a trigger arrangement adapted to hold and release the drive gear for rotary movement, wherein
respective abutments associated with the elongate threaded plunger and the dose setting element that move into a blocking configuration when said elongate plunger advances after successive doses to a final dose position, thereby preventing return of said rotary dose setting element to its latched, energized condition.

2. The injection apparatus according to claim 1, wherein said abutments comprise respective cooperable lugs on the elongate plunger and on the dose setting element, which cooperate to constrain rotation of said dose setting element.

3. The injection apparatus according to claim 1, including a housing having two relatively movable parts required to be moved relative to one another in an initialization step prior to actuation to deliver a dose, and including an anti-tamper arrangement to prevent said relative movement prior to release of the anti-tamper arrangement.

4. The injection device according to claim 3, wherein said anti-tamper arrangement comprises a removable package for containing at least part of said device and adapted to hold said movable parts against initialization movement, prior to removal of said package.

5. The injection device according to claim 4, wherein said anti-tamper arrangement comprises a removable spacer element disposed to prevent said initialization movement.

6. The injection device according to claim 5, wherein said removable spacer element comprises a tear off band.

7. The injection device according to claim 5, wherein said removable spacer element comprises a tear off label.

8. The injection apparatus according to claim 5, wherein said removable spacer element is integrally formed with one of said housing parts.

* * * * *